United States Patent
Hugg et al.

(10) Patent No.: US 10,534,096 B1
(45) Date of Patent: Jan. 14, 2020

(54) PHOTON SCATTER IMAGING

(71) Applicant: KROMEK GROUP, PLC, Sedgefield, County Durham (GB)

(72) Inventors: James William Hugg, Mars, PA (US); Ian Radley, Durham (GB)

(73) Assignee: KROMEK GROUP, PLC, Sedgefield, County Durham (GB)

( * ) Notice: Subject to any disclaimer, the term of this patent is extended or adjusted under 35 U.S.C. 154(b) by 0 days.

(21) Appl. No.: 16/016,215

(22) Filed: Jun. 22, 2018

(51) Int. Cl.
G01T 1/24 (2006.01)
A61B 6/03 (2006.01)
A61B 6/00 (2006.01)
A61B 6/04 (2006.01)

(52) U.S. Cl.
CPC .......... *G01T 1/247* (2013.01); *A61B 6/037* (2013.01); *A61B 6/0457* (2013.01); *A61B 6/4241* (2013.01); *A61B 6/4258* (2013.01); *A61B 6/485* (2013.01); *A61B 6/502* (2013.01); *G01T 1/249* (2013.01)

(58) Field of Classification Search
CPC ......... G01T 1/247; G01T 1/249; A61B 6/037; A61B 6/0457; A61B 6/4241; A61B 6/4258; A61B 6/485; A61B 6/502
See application file for complete search history.

(56) References Cited

U.S. PATENT DOCUMENTS

| 4,780,823 | A | 10/1988 | Stoub |
| 4,839,808 | A | 6/1989 | Koral |
| 5,293,195 | A | 3/1994 | Berlad |
| 5,390,225 | A | 2/1995 | Hawman |
| 5,434,414 | A | 7/1995 | Berlad |
| 5,438,202 | A | 8/1995 | Matanzon |
| 5,530,248 | A | 6/1996 | Natanzon |
| 5,818,050 | A * | 10/1998 | Dilmanian ............ G01T 1/1642 250/363.09 |
| 6,369,389 | B1 | 4/2002 | Berlad |
| 6,381,349 | B1 | 4/2002 | Zeng |

(Continued)

OTHER PUBLICATIONS

P Bloch, T Sanders, Reduction of the Effects of Scattered Radiation on a Sodium Iodide Imaging System, Journal of Nuclear Medicine, 1973, pp. 67-72, vol. 14, pub. by Society of Nuclear Medicine and Molecular Imagin g, Reston, VA.

(Continued)

*Primary Examiner* — Christine S. Kim
(74) *Attorney, Agent, or Firm* — Ference & Associates LLC

(57) ABSTRACT

One embodiment provides a method, including: receiving a dataset associated with a plurality of photon emission events interacting with a detector array of an imaging device; identifying a first subset of the dataset associated with a plurality of unscattered photon emission events from the plurality of photon emission events; identifying a second subset of the dataset associated with at least one scattered photon event from the plurality of photon emission events; determining, for a scattered photon event, a likely location of emission of the scattered photon event using data from the first subset of the dataset associated with the plurality of unscattered photon events; and correcting the dataset by associating the scattered photon event with the determined likely location of emission. Other aspects are described and claimed.

15 Claims, 6 Drawing Sheets

(56) References Cited

U.S. PATENT DOCUMENTS

| | | | |
|---|---|---|---|
| 7,888,651 B2 | 2/2011 | Chinn et al. | |
| 7,915,578 B2 | 3/2011 | Case | |
| 8,835,858 B2 | 9/2014 | Volokh et al. | |
| 2003/0094569 A1 | 5/2003 | Engdahl et al. | |
| 2008/0050000 A1* | 2/2008 | Blaffert | G06T 7/0012 |
| | | | 382/131 |
| 2009/0078876 A1* | 3/2009 | Chinn | G01T 1/2985 |
| | | | 250/363.04 |
| 2009/0206721 A1* | 8/2009 | Foret | H05H 1/24 |
| | | | 313/231.01 |
| 2010/0059682 A1* | 3/2010 | Conti | G01T 1/2985 |
| | | | 250/362 |
| 2012/0265050 A1* | 10/2012 | Wang | A61B 5/055 |
| | | | 600/411 |
| 2015/0331118 A1* | 11/2015 | Iltis | G01T 1/1647 |
| | | | 250/362 |
| 2016/0048615 A1* | 2/2016 | Kolthammer | G06T 11/005 |
| | | | 703/2 |
| 2018/0061089 A1* | 3/2018 | Rong | G06T 11/005 |

OTHER PUBLICATIONS

B Axelsson, P Msaki, A Israelsson, Subtraction of Scattered Photons in Single-Photon Emission Computerized Tomography, Journal of Nuclear Medicine, 1984, pp. 490-494, vol. 25, pub. by Society of Nuclear Medicine and Molecular Imagin g, Reston, VA.

SR Meikle, BF Hutton, DL Bailey, A Transmission-Dependent Method for Scatter Correction in SPECT, Journal of Nuclear Medicine, 1994, pp. 360-367, vol. 35, pub. by Society of Nuclear Medicine and Molecular Imagin g, Reston, VA.

FJ Beekman, Hwam Dejong, ETP Slijpen, Efficient SPECT Scatter Calculation in Non-Uniform Media Using Correlated Monte Carlo Simulation, Physics in Medicine and Biology, 1999, N183-N192, vol. 44, IOP Publishing, Bristol, UK.

E Vandervoort, Implementation of an Analytically Based Scatter Correction in SPECT Reconstructions, MS Thesis, University of British Columbia, 2000, 190 pages, Vancouver, BC, Canada.

A Sitek, SC Moore, MF Kijewski, Correction for Photon Attenuation Without Transmission Measurements Using Compton Scatter Information in SPECT, IEEE Nuclear Science Symposium Conference Record, M25-3, 2007, pp. 4210-4212, pub. by John Wiley and Sons, Hoboken, NJ.

P Ritt, H Vija, J Hornegger, T Kuwert, Absolute Quantification in SPECT, European Journal of Nuclear Medicine and Molecular Imaging, 2011, vol. 38(Suppl 1), pp. 69-77 pub. by Springer Verlag, New York, NY.

BF Hutton, I Buvat, FJ Beekman, Review and Current Status of SPECT Scatter Correction, Physics in Medicine and Biology, 2011, vol. 56, pp. R85-R112, IOP Publishing, Bristol, UK.

European Patent Office, European Search Report, dated Nov. 5, 2019, 7 pages.

Habib Zaidi et al., "Scatter modelling and compensatoin in emission tomography", European Journal of Nuclear Medicine and Molecular Imaging, vol. 31, No. 5, May 2004, 22 pages, Springer-Verlag.

* cited by examiner

PHOTON SCATTER IMAGING

BACKGROUND

Imaging devices perform many different functions such as medical imaging, security screening, image capture, or the like. The source of the imaging may be a radiological source, visible light, non-visible light, or any type of source for which the imaging device is capable of detection. For example, in a medical setting, a patient may be injected with a radiopharmaceutical tracer agent and the imaging device may capture the emission of gamma photon radiation from the patient's body for diagnostic analysis. The imaging device may include a gamma camera sensitive to the emission source, for example, a camera including a specific substance or object that is sensitive to or reacts to the emission source. The camera may contain individual pixels which may allow the imaging source to determine the location, energy, timing, and intensity of the emitted signal.

BRIEF SUMMARY

In summary, one aspect provides a method, comprising: receiving a dataset associated with a plurality of photon emission events interacting with a detector array of an imaging device; identifying a first subset of the dataset associated with a plurality of unscattered photon emission events from the plurality of photon emission events; identifying a second subset of the dataset associated with at least one scattered photon event from the plurality of photon emission events; determining, for a scattered photon event, a likely location of emission of the scattered photon event using data from the first subset of the dataset associated with the plurality of unscattered photon events; and correcting the dataset by associating the scattered photon event with the determined likely location of emission.

Another aspect provides an information handling device, comprising: a processor; a memory device that stores instructions executable by the processor to: receive a dataset associated with a plurality of photon emission events interacting with a detector array of an imaging device; identify a first subset of the dataset associated with a plurality of unscattered photon emission events from the plurality of photon emission events; identify a second subset of the dataset associated with at least one scattered photon event from the plurality of photon emission events; determine, for a scattered photon event, a likely location of emission of the scattered photon event using data from the first subset of the dataset associated with the plurality of unscattered photon events; and correct the dataset by associating the scattered photon event with the determined likely location of emission.

A further aspect provides a product, comprising: a storage device that stores code, the code being executable by a processor and comprising: code that receives a dataset associated with a plurality of photon emission events interacting with a detector array of an imaging device; code that identifies a first subset of the dataset associated with a plurality of unscattered photon emission events from the plurality of photon emission events; code that identifies a second subset of the dataset associated with at least one scattered photon event from the plurality of photon emission events; code that determines, for a scattered photon event, a likely location of emission of the scattered photon event using data from the first subset of the dataset associated with the plurality of unscattered photon events; and code that corrects the dataset by associating the scattered photon event with the determined likely location of emission.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
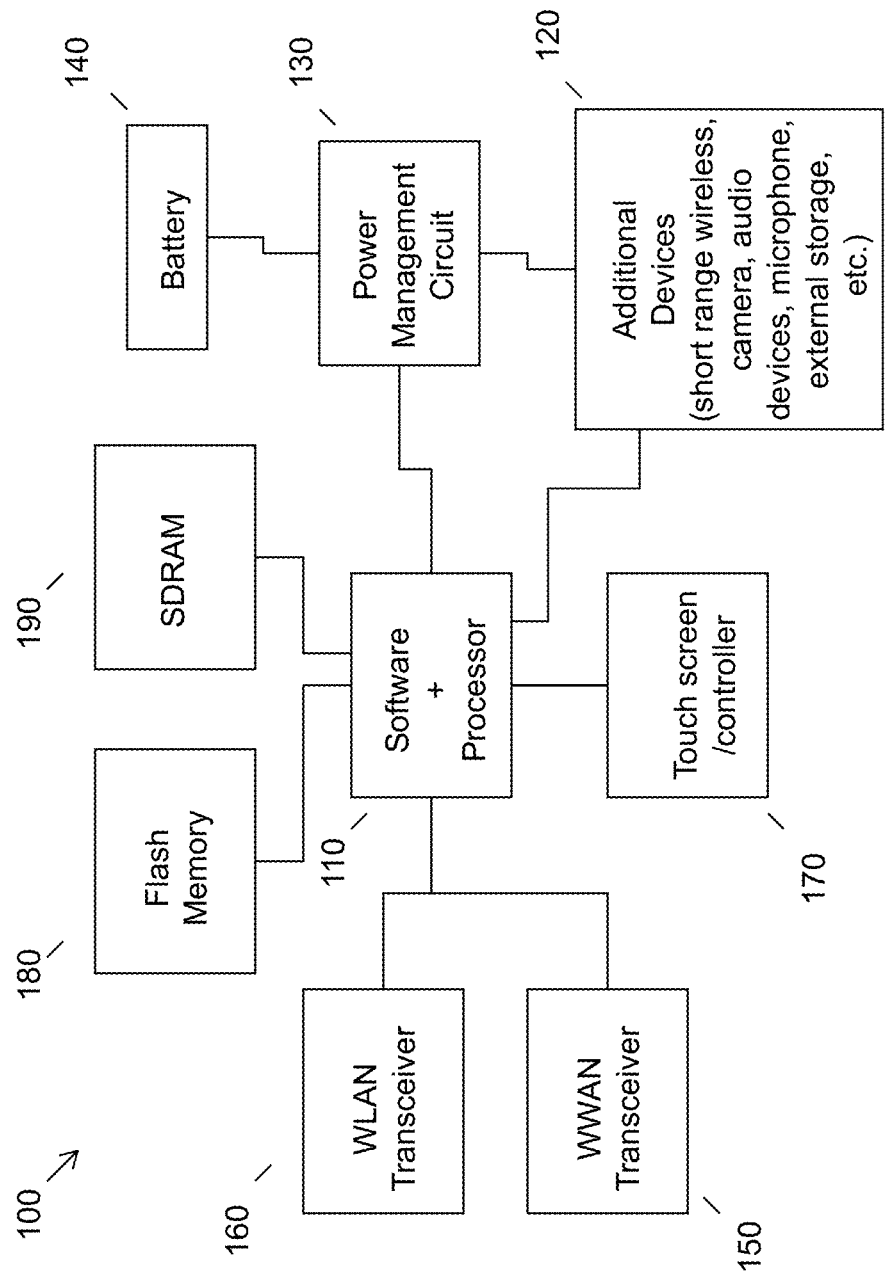
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Users of imaging devices often desire image output of a high spatial, temporal, and energy resolution. For example, a medical image having high spatial, temporal, and energy resolution may influence a patient's care by directing a physician to a location of interest within the patient's body. Many imaging devices utilize a camera sensitive to the type of emission being imaged in order to accurately capture an image. To capture the image, the camera image is divided into discrete areas or picture elements (pixels), where each pixel may represent both a location and an intensity within the image captured.

By way of illustration, in a nuclear medicine (molecular imaging) setting, a patient may be injected with a radiopharmaceutical tracer agent and the imaging device (gamma camera) may capture the emission of gamma photon radiation from the patient's body for diagnostic analysis. The detectors in a gamma camera may comprise a scintillator with coupled photon detectors (for example, photomultiplier tubes) or may comprise semiconductor direct-conversion materials such as CdZnTe, CdTe, HgI, and Si. A gamma photon detector pixel array comprising a semiconductor direct-conversion detector material has advantages over scintillator plus photon detector gamma cameras, including superior energy and spatial resolution. However, a disadvantage of all gamma cameras is a loss of signal due to Compton scattering of emission photons in the body of the patient during imaging. For example, in a medical imaging application such as SPECT (Single-Photon Emission Computed Tomography) gamma photons from an emission source within the body of the patient may be scattered by collision with tissue and bone between the point of emission and the imaging pixel in the gamma camera. Since image formation typically may require accepting counts only within an energy window closely surrounding the photopeak, scattered counts may be included in the image, producing a blurring effect. Typically, an estimate is made of the scatter component of the image, which can be up to 60% of the image counts in human patients, and scatter is subtracted from the image to produce a "scatter corrected" image, approximately comprising an image of only unscattered photon emissions. As will be apparent to those skilled in the art, a patient must be given a higher dose of a radioactive tracer because a significant fraction of the photon emission events detected by the gamma camera will be discarded as scatter during image reconstruction. This invention provides a novel solution to the loss of scatter data and allows more efficient detection using a smaller radiation dose or a shorter examination time or a combination of the two.

Currently, many SPECT imaging devices produce an image preferentially from unscattered photon events in which scattered photon events may be treated as noise or non-useful data. Therefore, photon events due to scatter within the patient may be completely ignored, resulting in a blurring and loss of image contrast, or discarded, if the scatter component can be estimated. In some systems, the energy resolution of the imaging device may not be high enough to cleanly separate unscattered events from scattered events, resulting in an image comprising both scattered and unscattered emission photons. What is needed is an efficient and high-energy-resolution imaging device that can detect scattered photon events and exploit these scattered events as useful data in the formation of photon emission images. The solution described herein may be used in a medical setting to reduce radiological dosing to patients, reduce imaging time, improve diagnosis, lower costs, improve patient outcomes, and provide better imaging data to healthcare professionals.

Accordingly, an embodiment provides a system and method of correcting an image by associating at least one scattered photon event with the location of a plurality of unscattered photon events. In an embodiment, an imaging device may receive a plurality of photon emission events including both unscattered and scattered photon emissions. The imaging system may reconstruct an image of the source locations in the patient's body that is predominantly due to the unscattered photon emissions. The imaging device may also identify at least one scattered photon emission event. In an embodiment, an image may be corrected by associating the at least one scattered photon emission event with the source location in the patient's body most likely associated with the scattered photon event. In an embodiment, a scattered photon emission event may be added to the image at or near the most likely source location in the patient's body. Other methods of associating at least one scattered photon emission event to the most likely source location are described and disclosed.

Such systems and methods provide a technical improvement to current imaging techniques. Rather than discarding or misreading scattered photon emission events, the embodiments as described herein capture useful clinical image information from both unscattered and scattered photon emission events. The system can identify a scattered photon emission event by its energy, which determines a range of Compton scattering angles, thereby providing a system and method for reconstructing images using the scattered photon emission events, rather than discarding them as unwanted image noise. These improvements may be important for medical imaging, lower patient dosing of imaging reagents, reduce exam/procedure time, or the like.

The illustrated example embodiments will be best understood by reference to the figures. The following description is intended only by way of example, and simply illustrates certain example embodiments.

One embodiment of scattered photon imaging applies to smart phones, tablets, and the like, that ubiquitously include a pixelated optical photography camera and display of the pixelated image. While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, I/O ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additionally, devices 120 are commonly included, e.g., an image sensor such as a camera. System 100 often includes a touch screen 170 for data input and display/rendering. System 100 also typically includes various memory devices, for example flash memory 180 and SDRAM 190. The components described herein may be adapted for use in an imaging device.

Figure 2:
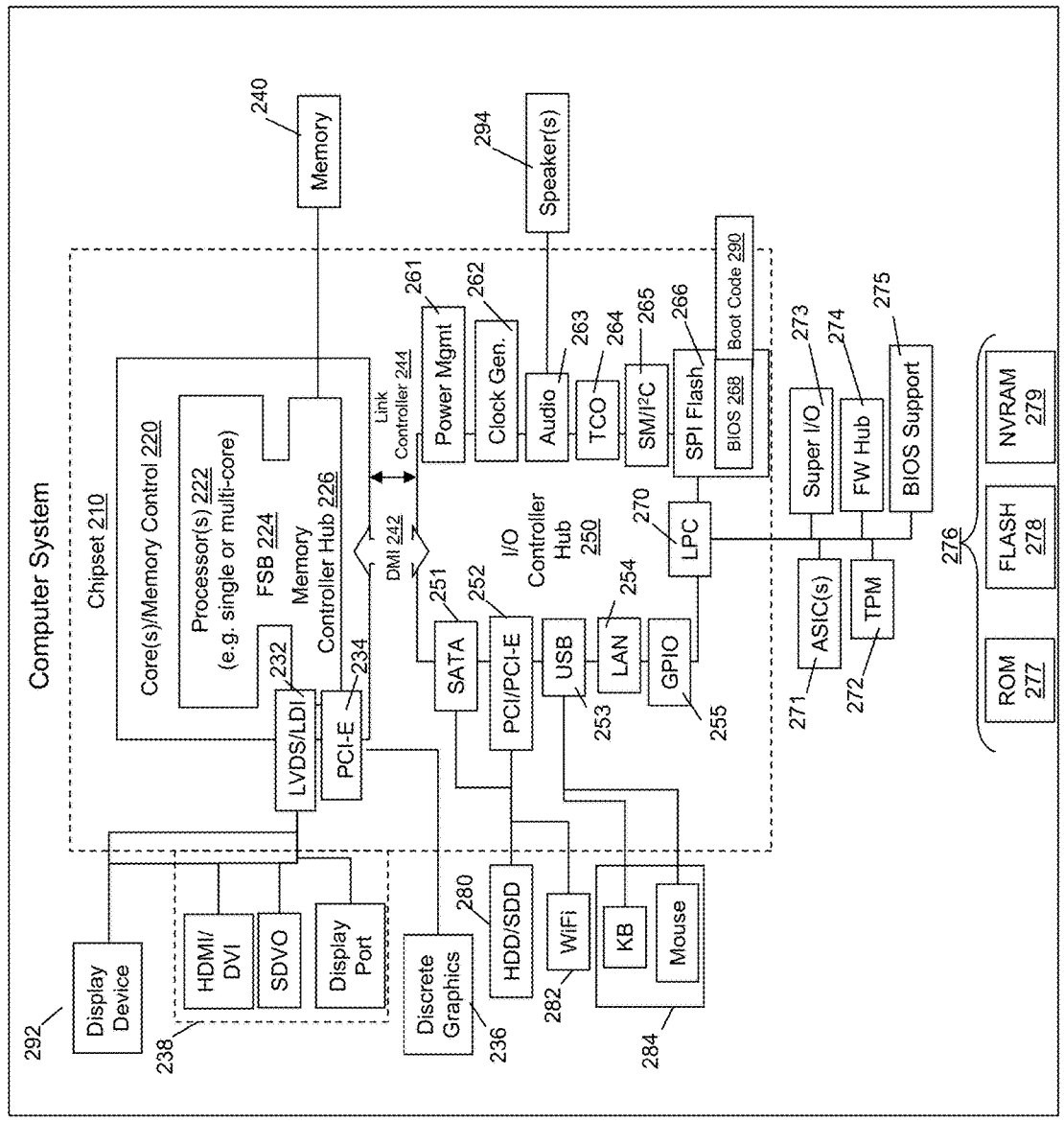
FIG. 2 illustrates another example of information handling device circuitry.

FIG. 2 depicts a block diagram of another example of information handling device circuits, circuitry or components. The example depicted in FIG. 2 may correspond to computing systems such as personal computers, laptop computers, or other devices that may embody imaging scattered photons detected by the pixelated digital cameras such devices ubiquitously comprise. The scatter imaging may also be performed on the computing system when it is attached to a gamma camera, such as in a medical imaging application. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer (for example, INTEL, AMD, ARM, etc.). INTEL is a registered trademark of Intel Corporation in the United States and other countries. AMD is a registered trademark of Advanced Micro Devices, Inc. in the United States and other countries. ARM is an unregistered trademark of ARM Holdings plc in the United States and other countries. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of RAM that may be referred to as "system memory" or "memory"). The memory controller hub 226 further includes a low voltage differential signaling (LVDS) interface 232 for a display device 292 (for example, a CRT, a flat panel, touch screen, etc.). A block 238 includes some technologies that may be supported via the LVDS interface 232 (for example, serial digital video, HDMI/DVI, display port). The memory controller hub 226 also includes a PCI-express interface (PCI-E) 234 that may support discrete graphics 236.

In FIG. 2, the I/O hub controller 250 includes a SATA interface 251 (for example, for HDDs, SDDs, etc., 280), a PCI-E interface 252 (for example, for wireless connections 282), a USB interface 253 (for example, for devices 284 such as a digitizer, keyboard, mice, cameras, phones, microphones, storage, other connected devices, etc.), a network interface 254 (for example, LAN), a GPIO interface 255, a LPC interface 270 (for ASICs 271, a TPM 272, a super I/O 273, a firmware hub 274, BIOS support 275 as well as various types of memory 276 such as ROM 277, Flash 278, and NVRAM 279), a power management interface 261, a clock generator interface 262, an audio interface 263 (for example, for speakers 294), a TCO interface 264, a system management bus interface 265, and SPI Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices such as tablets, smart phones, personal computer devices generally, and/or electronic devices which users may use in or with systems as described herein. For example, the circuitry outlined in FIG. 1 may be implemented in a tablet or smart phone embodiment, whereas the circuitry outlined in FIG. 2 may be implemented in a personal computer embodiment.

Figure 3:
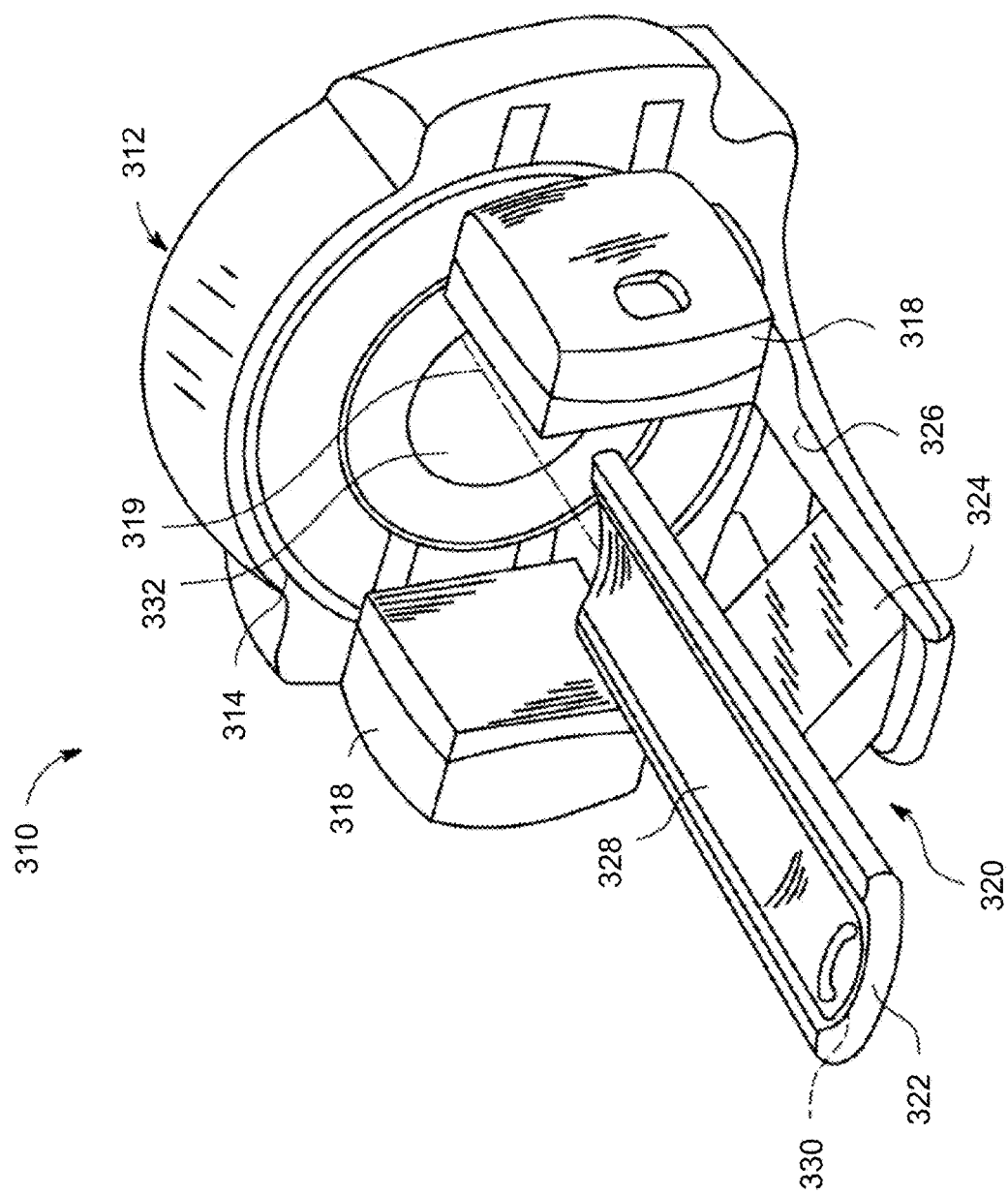
FIG. 3 illustrates another embodiment of an imaging device that may use the disclosed embodiments.

Referring to FIG. 3, the pixelated detectors and/or gamma cameras of the various embodiments may be provided as part of different types of imaging systems, for example, nuclear medicine (NM) imaging systems such as positron emission tomography (PET) imaging systems, single-photon emission computed tomography (SPECT) imaging systems and/or x-ray imaging systems and x-ray computed tomography (CT) imaging systems, among others. For example, FIG. 3 is a perspective view of an exemplary embodiment of a medical imaging system 310 constructed in accordance with various embodiments, which in this exemplary embodiment is a SPECT imaging system. The system 310 includes an integrated gantry 312 that further includes a rotor 314 oriented about a gantry central bore 332. The rotor 314 is configured to support one or more NM pixelated cameras 318 and associated collimators 317 (two cameras 318 and two collimator 317 are shown), such as, but not limited to gamma cameras, SPECT detectors, multi-layer pixelated cameras (e.g., Compton camera) and/or PET detectors. It should be noted that when the medical imaging system 310 includes a CT camera or an x-ray camera, the medical imaging system 310 also includes an x-ray tube (not shown) for emitting x-ray radiation towards the detectors. In various embodiments, the cameras 318 are formed from pixelated detectors as described in more detail herein. The rotors 314 are further configured to rotate axially about an examination axis 319.

A patient table 320 may include a bed 322 slidingly coupled to a bed support system 324, which may be coupled directly to a floor or may be coupled to the gantry 312 through a base 326 coupled to the gantry 312. The bed 322 may include a stretcher 328 slidingly coupled to an upper surface 330 of the bed 322. The patient table 320 is configured to facilitate ingress and egress of a patient (not shown) into an examination position that is substantially aligned with examination axis 319 and in which the patient is located in the field of view of the gamma cameras 318. During an imaging scan, the patient table 320 may be controlled to move the bed 322 and/or stretcher 328 axially into and out of a bore 332. The operation and control of the imaging system 310 may be performed in any manner known in the art. It should be noted that the various embodiments may be implemented in connection with imaging systems that include rotating gantries or stationary gantries.

Figure 4:
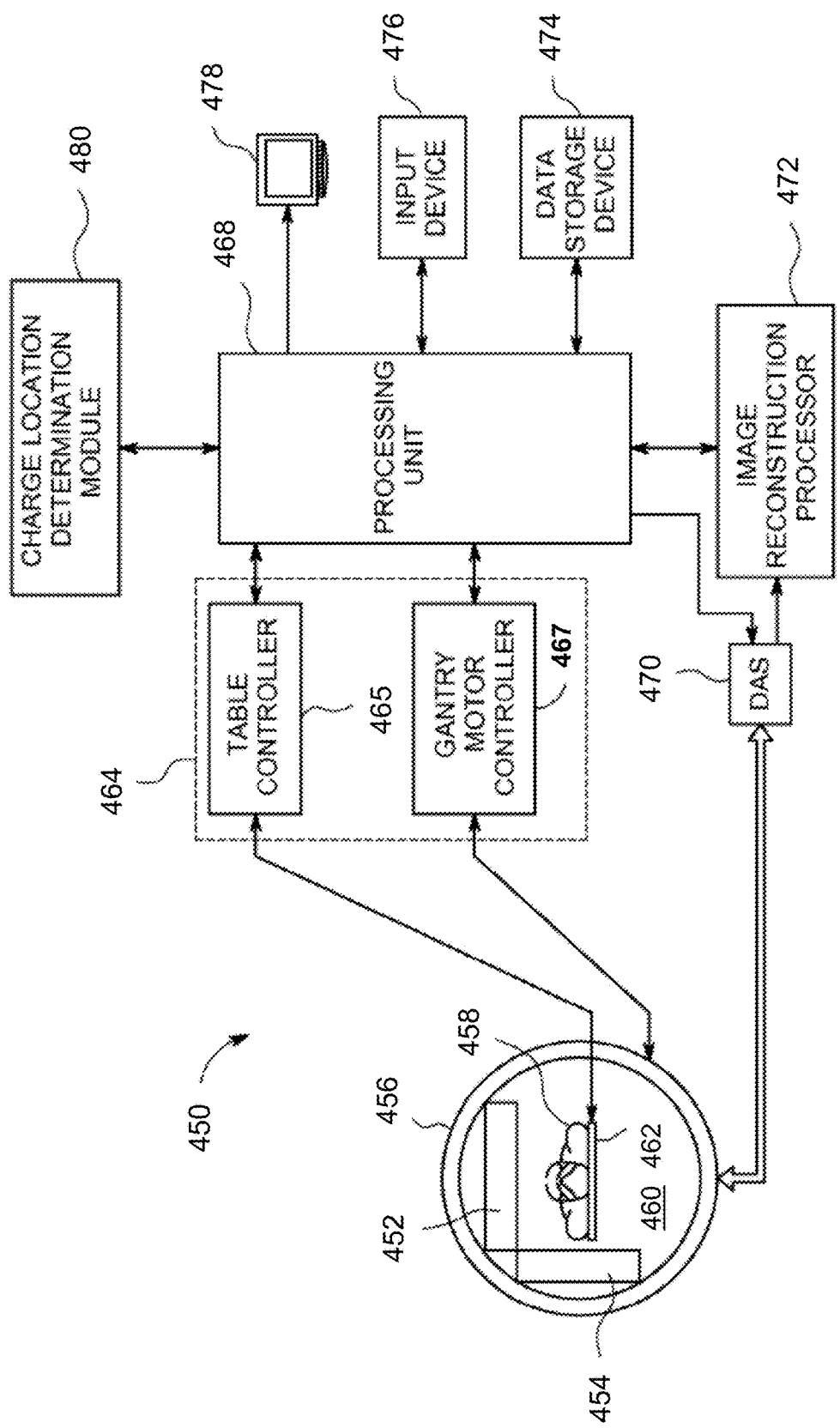
FIG. 4 illustrates a further example of information handling device circuitry for the example imaging device of FIG. 3 that may use the disclosed embodiments.

Referring now to FIG. 4 which illustrates a block diagram illustrating an imaging system 450 that has a plurality of pixelated imaging detectors and/or gamma cameras configured in accordance with various embodiments mounted on a gantry. It should be noted that the imaging system may also be a multi-modality imaging system, such as an NM/CT imaging system. The imaging system 450, illustrated as a SPECT imaging system, generally includes a plurality of pixelated imaging detectors 452 and 454 (two are illustrated) mounted on a gantry 456. It should be noted that additional imaging detectors may be provided. The imaging detectors 452 and 454 are located at multiple positions (e.g., in an "L-mode" 90 degree configuration, as shown) with respect to a patient 458 in a bore 460 of the gantry 456. The patient 458 is supported on a patient table 462 such that radiation or imaging data specific to a structure of interest (e.g., the heart) within the patient 458 may be acquired. It should be noted that although the imaging detectors 452 and 454 are configured for movable operation (azimuthally around, radially in or out, rotatably around an axis, tiltably about a pivot, and the like) of the gantry 456, in some imaging systems, imaging detectors are fixedly coupled to the gantry 456 and in a stationary position, for example, in a PET imaging system (e.g., a ring of imaging detectors). It also should be noted that the imaging detectors 452 and 454 may be formed from different materials as described herein and provided in different configurations known in the art, such as flat or curved panels.

One or more collimators may be provided in front of the radiation detection face (317 in FIG. 3, but not shown in FIG. 4) of one or more of the imaging detectors 452 and 454. The imaging detectors 452 and 454 acquire a 2D image that may be defined by the x and y location of a pixel and the location of the imaging detectors 452 and 454. The radiation detection face (not shown) is directed towards, for example, the patient 458, which may be a human patient, animal, airport baggage, or the like.

A controller unit 464 may control the movement and positioning of the patient table 462 with respect to the imaging detectors 452 and 454 and the movement and positioning of the imaging detectors 452 and 454 with respect to the patient 458 to position the desired anatomy of the patient 458 within the fields of view (FOVs) of the imaging detectors 452 and 454, which may be performed prior to acquiring an image of the anatomy of interest. The controller unit 464 may have a table controller 465 and a gantry motor controller 467 that each may be automatically commanded by a processing unit 468, manually controlled by an operator, or a combination thereof. The table controller 465 may move the patient table 462 to position the patient 458 relative to the FOVs of the imaging detectors 452 and 454. Additionally, or optionally, the imaging detectors 452 and 454 may be moved, positioned or oriented relative to the patient 458 or rotated about the patient 458 under the control of the gantry motor controller 467.

The imaging data may be combined and reconstructed into an image, which may comprise 2D images, a 3D volume or a 3D volume over time (4D).

A Data Acquisition System (DAS) 470 receives analog and/or digital electrical signal data produced by the imaging detectors 452 and 454 and decodes the data for subsequent processing as described in more detail herein. An image reconstruction processor 472 receives the data from the DAS 470 and reconstructs an image using any reconstruction process known in the art. A data storage device 474 may be provided to store data from the DAS 470 or reconstructed image data. An input device 476, such as a keyboard, mouse, touchscreen, or the like also may be provided to receive user inputs and a display 478 may be provided to display reconstructed images. A charge location determination module 480 may provide x and y position for each gamma photon interaction with the pixelated imaging detectors 452 and 454. In an embodiment, a depth-of-interaction z position may be determined.

In an embodiment, the imaging device may be installed in a location for security scanning. For example, the device may be in an airport security checkpoint, a baggage screening location, or the like. The device may comprise a plurality of x-ray sources and a plurality of pixelated photon detector arrays. In an embodiment, the imaging device may be permanently anchored, moveable, or completely portable. For example, an imaging device may be a hand-held device for use by first responders, security, or assessment teams. Other uses outside of a security setting are contemplated and are disclosed. As should be understood by one skilled in the art, both healthcare imaging and security screening are merely examples. Other possible applications for the techniques as described herein are possible and contemplated.

In an embodiment, the receiving equipment may contain sensors that are sensitive to radiological particles or photons. The receiving equipment may record communication events, also referred to as interactions, on an array of sensors located in the receiving equipment. Each of the sensors in the array may be represented as a pixel in the final image. During the course of imaging, a photon or particle may strike one or more pixel detection units. In an embodiment, the signals received from the one or more pixel detection units may be used to separate unscattered and scattered photon emissions and to reconstruct an image using both. In a healthcare setting this may allow healthcare professionals to achieve better imaging in less time and with less radiolabel dose delivered to a patient which may result in better treatment plans and decrease medical costs, for example, better efficiency may be achieved and imaging sessions' durations may be reduced.

Figure 5:
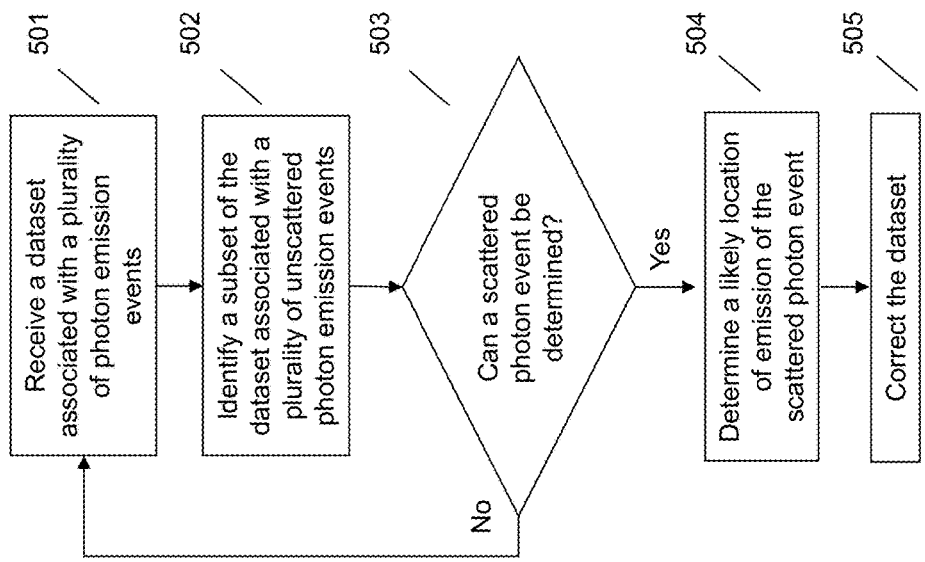
FIG. 5 illustrates a method of determining a scattered event within an image.

Referring now to FIG. 5, an embodiment of an imaging device and method may be in a healthcare setting, security screening, manufacturing, or any application where an imaging device may be utilized. For example, the imaging device may be a radiological imaging device in which radiological matter (consisting of particles or photons) is either transmitted through or injected into and emitted from a patient's body. Another example may include an airport or port of entry device used to scan for radiation or other material of interest for security purposes. Another example of an imaging device may be used by first responder to determine environmental conditions and/or safety of a location. Other uses are contemplated and disclosed.

At step 501 an embodiment may acquire one or more projection images of photon emissions. Acquiring an image may comprise receiving or capturing a communication event occurring within a photon detector pixel array. Receiving or capturing an interaction may include receiving one or more signals from one or more pixel detection units that indicate an interaction has occurred. For readability, the discussion herein will refer to a photon as that object which is causing the interaction and resulting in the signals. However, it should be understood that the object may include a photon (light of any spectrum), a radiological particle, or any type of energy which the detection unit is capable of detecting. A photon detector pixel array may be one or more pixel detector units. A photon detector pixel array may be organized in any configuration such as a grid, a brick pattern, an interspersed pattern, or the like. The photon detector pixel array may be oriented in a flat plane, curved plane, or the like. In other words, the photon detector pixel array may be arranged in a manner that is suitable for detecting interactions from an emission source and may be different for different applications. For example, a photon from an emission source may interact with one or more pixels on a photon pixel array as part of an imaging unit in a medical setting. A plurality of projection images is acquired in SPECT imaging. For example, in a system 310 such as that depicted in FIG. 3, the gantry may rotate 6 degrees between each set of two projection images (one for each gamma camera 318)

until a total of 60 projection images have been acquired. Each of these projection images may be processed to make corrections for attenuation and/or scatter before being further processed to reconstruct a 3D image of the patient's body, particularly showing the distribution of an injected (or ingested or inhaled) radioisotope tracer.

In an embodiment a pixel (picture element) refers to a discrete location on the imaging hardware surface that may be only a subset of the imaged area. The data or electronic communication from a pixel or plurality of pixels may be used to form an image as a composite from the one or more pixels. An imaging device may use many methods to detect a communication event from a pixel. For example, in a consumer camera a pixel represents the intensity and wavelength of the visible light detected by the pixel. As another example, radiological imaging devices used in cancer screenings, radiation detectors, and the like, use a type of atomic particle or photon emitted by a source and measurable by a sensor with associated circuitry to provide both a location, energy, and intensity (or count density) of the radiological particles or photons detected. Using the communication events from the pixels, an image may be created based upon the location, intensity, and energy or wavelength of the communication event from the pixel. In other words, an embodiment may use the signal transmitted from the pixel during imaging to create an image based upon the information contained within the signal. The data may be collected from multiple pixels to create an image of a larger area.

In an embodiment with a semiconductor detector material, a photon detector pixel array may have two sides with metallic electrodes deposited on the semiconductor detector crystal. A first side may comprise a plurality of pixels, also referred to as the pixelated side, which may be arranged in a grid pattern. This side may be coupled to read-out electronics that can capture the signal from the pixelated side. In the case of CdZnTe (CZT) or CdTe, in which the electron mobility is much larger than hole mobility, the pixelated side may be the anode side of the array and provide anode signals. In some configurations, this side may be connected to ground potential. In an embodiment, a second side of the detector pixel array may be substantially opposite the first side, for example, in the case of a thick sheet-like detector, the first side may be the bottom side, and the second side may be the top side, typically the side from which gamma photons may be incident upon the detector. This second side of the detector pixel array may be a cathode and may be connected to a negative voltage bias.

At step 502 an embodiment may estimate the scatter fraction in the photopeak energy window for each pixel in each projection image, and then subtract the estimated number of scattered photon emission events from each pixel. Several possible methods for estimating scatter fraction are discussed below.

At step 503 an image of the emission source locations within a patient's body may be reconstructed from a plurality of projection images. Because the scatter fraction was estimated and subtracted at step 502, the resulting reconstructed image is labelled as "scatter-corrected." This type of image is typically produced in commercial SPECT systems, often with additional corrections for attenuation and resolution recovery. In a solid-state semiconductor photon detector pixel array, the energy resolution may be very good. For example, in CZT detectors, the energy resolution may be 3-4% FWHM (full-width at half maximum of the photopeak) at 140 keV, much better in comparison with a NaI scintillator detector with energy resolution of about 10% FWHM at 140 keV. The superior energy resolution enables more effective discrimination between scattered photon emissions and unscattered photon emissions, because the scattered photons always have lower energy than the unscattered photons. This will be highlighted in the discussion below of FIG. 6.

The predominantly unscattered photon emission events may be reconstructed into an image of the photon emission source locations within the patient's body. The SPECT image reconstruction may be any method known in the art, including filtered back-projection (FBP), MLEM (Maximum Likelihood Expectation Maximization) or OSEM (Ordered Subset Expectation Maximization), or ART (Algebraic Reconstruction Technique), and other iterative algebraic, iterative statistical, and iterative learned reconstruction methods. The image may be corrected for the presence of scattered photon emission events by estimating the scattered component of the image and subtracting the estimate from the original image. This will be a more efficient part of the process when semiconductor photon detector pixel arrays are used with their superior energy resolution. Far fewer scattered photon events will be mixed with the unscattered photon events, so it is easier to separate the scattered events and reconstruct a predominantly unscattered image of the source locations of unscattered photon emissions.

Figure 6:
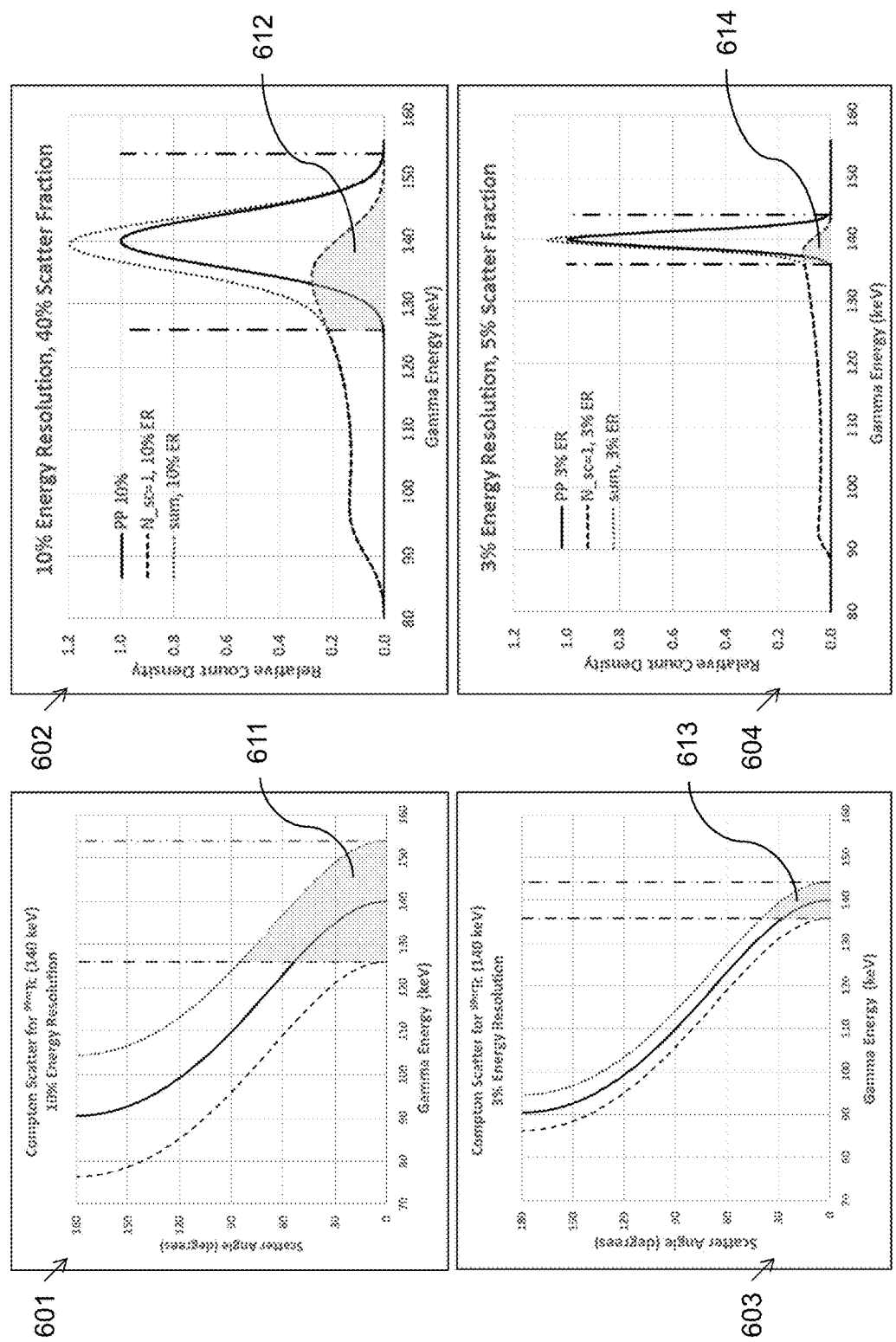
FIG. 6 illustrates examples of scatter angle and relative count density with respect to gamma energy and energy resolution.

For example, FIG. 6 illustrates several graphs of gamma photon emission events with Compton scatter in the patient's body before detection by a gamma camera. The graphs are computed using the well-known Compton scattering formula:

$$E_{SC} = \frac{E_0}{1 + (E_0/m_e c^2)(1 - \cos\theta)},$$

where $E_0$ is the energy of the gamma photon emission, typically 140 keV for $^{99m}$Tc, a common isotope for medical imaging, $E_{sc}$ is the energy of the scattered gamma photon, $m_e c^2$ is the rest energy of an electron, 511 keV, from which the emitted gamma photon scatters, and $\theta$ is the scattering angle. The top two graphs 601 and 602 illustrate the effect of Compton scatter on a typical NaI scintillator gamma camera where the energy resolution may be about 10% FWHM (14 keV for the 140 keV photopeak). The bottom two graphs 603 and 604 illustrate the effect of Compton scatter on a CZT pixelated gamma camera where the energy resolution may be about 3% FWHM (4 keV for the 140 keV photopeak). In SPECT imaging, detected photon events within an energy window centered on the photopeak with width of about ±FWHM are included in the image. In the top two graphs 601 and 602, the imaging energy window consists of all detected photon events between the two vertical dashed lines at 140−14=126 keV and 140+14=154 keV. Similarly, for the bottom two graphs 603 and 604, the energy window consists of all detected photon events between the two vertical dashed lines at 140−4=136 keV and 140+4=144 keV.

In FIG. 6, the two graphs on the right 602 and 604 illustrate the energy spectra (relative count density as a function of gamma photon energy) for both unscattered photons (solid Gaussian shaped peaks) and the singly-scattered photons (heavy dashed curves). The shape of the scattered photon spectra was calculated using the well-known Klein-Nishina formula, convolved with the Gaussian with either 10% FWHM (for 602) or 3% FWHM (for 604).

Of course, the scattered photons can scatter multiple times before exiting the patient's body and interacting with the photon detector array, but the key aspect of the invention is apparent by considering only a single scatter event. The light gray-shaded areas 611, 612, 613, and 614 represent the scattered photons that are detected within the energy windows that may be used for image formation. As noted in the title of the graph 602, when the energy resolution is about 10% (scintillator gamma cameras), the fraction of events from a single Compton scatter within the patient can be about 40% of the total detected spectrum (dotted line peak) in this illustrative calculation. The title of graph 604 similarly discloses that when the energy resolution is about 3% (CZT gamma cameras), the fraction of events from a single Compton scatter within the patient can be about 5% of the total detected spectrum (dotted line peak) in this illustrative calculation. Clearly the superior energy resolution of a CZT gamma camera benefits SPECT imaging by including substantially less scattered photons in the photopeak image. This benefit of superior energy resolution can be used to enable the invention we describe herein.

In FIG. 6, the two graphs on the left 601 and 603 illustrate the Compton scattering angle in degrees as a function of the energy of the scattered gamma photon. The gray-shaded region 611 in graph 601 includes scatter in the imaging window at scatter angle up to almost 90 degrees due in part to a scatter window of about ±10% (scintillator gamma cameras) of the photopeak energy of 140 keV. Therefore, scatter events may be included in the energy window resulting in a reconstructed image which may be blurry and have reduced contrast because of the scattered photon emission events mixed in with the unscattered photon emission events. Previous methods may attempt to simply subtract scattered photon emission events from an image. The gray-shaded region 613 in graph 603 includes scatter in the imaging window at scatter angle below 40 degrees due in part to a scatter window of about ±3% (CZT gamma cameras) of the photopeak energy of 140 keV.

Now consider in graphs 602 and 604 that there are scattered photon emission events at energies below the lower bound of the photopeak energy window. Those scattered photons may be used to estimate the scatter fraction within the photopeak energy window, in order to subtract those counts, on a pixel-by-pixel basis. There may be other methods, such as Monte Carlo simulations based on the attenuation map derived from an x-ray CT (Computerized Tomography) or MRI (Magnetic Resonance Imaging) scan of the patient, or ray-tracing modeling, such as GEANT, that estimate the scattered photon contribution to the image at each pixel so that it can be subtracted and thrown away. The superior energy resolution of a gamma camera employing semiconductor (such as CZT) pixelated photon detector arrays enables a new option that is superior to all the methods that throw away scattered photons. Consider graphs 601 and 603 in the energy region below the lower bound of the photopeak energy window. In graph 601 for 10% energy resolution (scintillator gamma camera) a scattered photon detected at an energy of 110 keV will be associated with a range of scattering angles from about 60 to 130 degrees, an uncertainty of about 70 degrees. In contrast, in graph 603 for 3% energy resolution (CZT gamma camera) a scattered photon detected at an energy of 110 keV will be associated with a range of scattering angles from about 80 to 100 degrees, an significantly reduced uncertainty of only about 20 degrees. Thus, better energy resolution, as available with CZT gamma cameras, results in a much better estimate of the scattering angle, which in turn results in the ability to predict the location within the patient's body where the scattered photon emission originated.

Returning now to FIG. 5, at step 504 an embodiment may use the full energy spectra projection images to reconstruct a "scatter-included" 3D image. This is the step that differentiates this invention from any of the commercial SPECT systems that only produce "scatter-corrected" (that is, subtracted) images. It is important that the projection images comprise a full energy spectrum for each pixel, as this spectral information is required for using the scattered photons to enhance the reconstructed image. Notice that an arrow now connects the original uncorrected projection image data at 501 to the scatter-included reconstruction at 504. The scatter corrected image produced at 503 is based upon a photopeak energy window with the estimated scatter fraction in that window subtracted. This new scatter-included image uses the scatter-corrected image 503 as an input to the iterative image reconstruction process, but also uses the original uncorrected projection images at 501 to build a 3D image of the distribution of photon emission sources within the patient's body. This requires that the image reconstruction algorithm models the physical process of Compton scattering, as well as other physical processes, such as attenuation and collimator-detector response.

It would be simpler to identify the scattered photon emission events if we could assume that all unscattered photon emission events were confined to the photopeak energy window. This is not the case for a pixelated photon detector array comprising CZT direct conversion detectors. There is a fraction of the photon emission events that interact with the CZT detectors that will result in charge collection on more than one pixel. This may occur, for example, because the electron charge cloud is near the edge of a pixel and the charge collection is shared between two or more pixels. Two or more pixels may record an interaction because an initial Compton scatter occurs in one pixel and the final photoelectric interaction occurs in a different pixel. There may be a depth-of-interaction dependent collection of charge, due to a limited lifetime and mobility of either the electron or hole charges. These and other physical mechanisms may lead to a low energy spectral tail in a CZT detector. The effect is that some of the unscattered photon events which belong in the photopeak energy window may be recorded at lower energies where scattered photon emission events are expected. It is possible to identify charge sharing and depth-of-interaction dependent events and to correct their apparent energy to place them into the photopeak energy window, where they belong. If such corrections are performed, then the remaining events at energies below the lower bound of the photopeak energy window should be predominantly photon emissions that scattered in the patient's body. At photon emission energies higher than typical clinical SPECT radioisotopes, a significant number of the high energy gamma photons will Compton scatter in the CZT detector and then the scattered photon will escape from the detector without depositing its remaining energy, leading to a Compton plateau in the energy spectrum, representing photon emission events that may or may not have been scattered in the patient's body. However, this is a small effect at the energies of typical clinical SPECT radioisotopes.

At step 505, the method or system may correct an image by associating one or more scattered photon emission events with the location in the patient of the source of one or more unscattered photon emission events. In other words, an embodiment may identify scattered photon emission events and add the scattered events to a location in the image that is the most likely location in the patient for the photon emission before it was scattered. Scattered photon emission events may be counted as full events, equal in information content to unscattered events. Alternatively, a compensation may be made for scattered events to give them a value less than unscattered events in the image reconstruction.

The various embodiments described herein thus represent a technical improvement to imaging devices that may require high sensitivity and resolution to the material imaged. An embodiment allows for the association of scattered photon emission events with the source locations in the patient's body of unscattered photon emission events. Using the techniques described herein, the detection efficiency of the system can be substantially improved, so that rather than requiring longer imaging sessions and/or higher radiological doses, a more complete image may be achieved with lower imaging session durations and/or lower radiological doses. By more effectively removing the scatter background and assigning it to the appropriate source distribution for photon emissions, the image contrast and spatial resolution can be substantially improved. Such a system results in more accurate imaging, less device down-time, and lower costs associated with the imaging procedure. Image quantitation may also be improved by using scattered photons as well as unscattered photons, thus resulting in more accurate SUV (Standardized Uptake Value) estimation in SPECT.

The medical modality of SPECT has been used in this description of the invention for illustration. As will be appreciated by one skilled in the art, other medical, security, or non-destructive testing applications may also benefit from this invention. SPECT and PET are photon emission modalities; in contrast, photon transmission modalities such as x-ray CT, x-ray fluorescence, x-ray mammography, and x-ray radiography may use the method described to improve performance, including at least one of detection efficiency, image contrast, spatial resolution, and image quantitation.

As will be appreciated by one skilled in the art, various aspects may be embodied as a system, method or product device. Accordingly, aspects may take the form of an entirely hardware embodiment or an embodiment including software that may all generally be referred to herein as a "circuit," "module" or "system." Furthermore, aspects may take the form of a product device embodied in one or more device readable medium(s) having device readable program code embodied therewith.

It should be noted that the various functions described herein may be implemented using instructions stored on a readable storage medium device such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
receiving a dataset associated with a plurality of photon emission events interacting with a detector array of an imaging device, wherein the dataset contains at least one characteristic of each of the plurality of photon emission events including a spatial position and an energy identified using single photon emission computed tomography;
identifying a first subset of the dataset associated with a plurality of unscattered photon emission events from the plurality of photon emission events;
identifying a second subset of the dataset associated with at least one scattered photon event from the plurality of photon emission events, wherein the identifying a second subset of the dataset associated with at least one scattered photon event comprises estimating a scatter fraction in the photopeak energy window for each pixel within the received image;

determining, for a scattered photon event, a likely location of emission of the scattered photon event using data from the first subset of the dataset associated with the plurality of unscattered photon events based upon the at least one characteristic;

correcting the dataset by associating the scattered photon event with the determined likely location of emission; and providing, to a system, an image generated from the corrected dataset.

2. The method of claim 1, wherein the determining a likely location of emission comprises calculating a spatial distribution of the unscattered photon emission events.

3. The method of claim 1, wherein the detector array comprises an array of pixelated semiconductor detectors selected from the group consisting of: CdZnTe, CdTe, HgI, Si, and direct-conversion materials.

4. The method of claim 1, wherein the correcting the dataset comprises performing iterative image reconstruction with scatter included using an algorithm selected from the group consisting of: iterative algebraic, iterative statistical, and iterative learned reconstruction methods.

5. The method of claim 4, wherein the performing iterative image reconstruction with scatter included comprises modeling Compton scattering within at least one projection selected from the group consisting of: forward projections and back projections of the iterative image reconstruction algorithm.

6. The method of claim 1, wherein the determining a likely location of emission comprises accessing a model of an imaged subject.

7. The method of claim 6, wherein the identifying a second subset of the dataset associated with at least one scattered photon event comprises using the accessed model to identify projected imaging locations of scattered photon events.

8. An information handling device, comprising:
a processor;
a memory device that stores instructions executable by the processor to:
receive a dataset associated with a plurality of photon emission events interacting with a detector array of an imaging device, wherein the dataset contains at least one characteristic of each of the plurality of photon emission events including a spatial position and an energy identified using single photon emission computed tomography;
identify a first subset of the dataset associated with a plurality of unscattered photon emission events from the plurality of photon emission events;
identify a second subset of the dataset associated with at least one scattered photon event from the plurality of photon emission events, wherein the identifying a second subset of the dataset associated with at least one scattered photon event comprises estimating a scatter fraction in the photopeak energy window for each pixel within the received image;
determine, for a scattered photon event, a likely location of emission of the scattered photon event using data from the first subset of the dataset associated with the plurality of unscattered photon events based upon the at least one characteristic;

correct the dataset by associating the scattered photon event with the determined likely location of emission; and provide, to a system, an image generated from the corrected dataset.

9. The device of claim 8, wherein the determining a likely location of emission comprises calculating a spatial distribution of the unscattered photon emission events.

10. The device of claim 8, wherein the detector array comprises an array of pixelated semiconductor detectors selected from the group consisting of: CdZnTe, CdTe, HgI, Si, and direct-conversion materials.

11. The device of claim 8, wherein the correcting the dataset comprises performing iterative image reconstruction with scatter included using an algorithm selected from the group consisting of: iterative algebraic, iterative statistical, and iterative learned reconstruction methods.

12. The device of claim 11, wherein the performing iterative image reconstruction with scatter included comprises modeling Compton scattering within at least one projection selected from the group consisting of: forward projections and back projections of the iterative image reconstruction algorithm.

13. The device of claim 8, wherein the determining a likely location of emission comprises accessing a model of an imaged subject.

14. The device of claim 13, wherein the identifying a second subset of the dataset associated with at least one scattered photon event comprises using the accessed model to identify projected imaging locations of scattered photon events.

15. A product, comprising:
a storage device that stores code, the code being executable by a processor and comprising:
code that receives a dataset associated with a plurality of photon emission events interacting with a detector array of an imaging device, wherein the dataset contains at least one characteristic of each of the plurality of photon emission events including a spatial position and an energy identified using single photon emission computed tomography;
code that identifies a first subset of the dataset associated with a plurality of unscattered photon emission events from the plurality of photon emission events;
code that identifies a second subset of the dataset associated with at least one scattered photon event from the plurality of photon emission events, wherein the identifying a second subset of the dataset associated with at least one scattered photon event comprises estimating a scatter fraction in the photopeak energy window for each pixel within the received image;
code that determines, for a scattered photon event, a likely location of emission of the scattered photon event using data from the first subset of the dataset associated with the plurality of unscattered photon events based upon the at least one characteristic;
code that corrects the dataset by associating the scattered photon event with the determined likely location of emission; and
code that provides, to a system, an image generated from the corrected dataset.

* * * * *